United States Patent [19]

Coulson

[11] 4,440,726
[45] Apr. 3, 1984

[54] APPARATUS FOR ELECTROCHEMICAL DETECTION AND COULOMETRIC TITRATION

[76] Inventor: Dale M. Coulson, 21 Willow Rd., Apt. 13, Menlo Park, Calif. 94025

[21] Appl. No.: 458,305

[22] Filed: Jan. 17, 1983

[51] Int. Cl.³ .......................................... G01N 31/08
[52] U.S. Cl. ...................... 422/89; 422/68; 422/80; 422/83; 422/98; 436/52; 436/150; 436/163; 204/405; 204/411; 324/DIG. 1; 324/443
[58] Field of Search ...... 422/68, 82, 83, 89, 422/90, 98, 80; 436/51, 52, 53, 149, 150, 163; 73/26; 204/405, 409, 411 TE; 324/443, 445, 442, DIG. 1

[56] References Cited

U.S. PATENT DOCUMENTS

| 2,876,189 | 3/1959 | Spracklen | 422/68 X |
| 3,658,679 | 4/1972 | Stansell et al. | 204/409 |
| 4,085,009 | 4/1978 | Pace | 204/1 E |

Primary Examiner—Michael S. Marcus
Assistant Examiner—Michael S. Gzybowski

Attorney, Agent, or Firm—Willis E. Higgins

[57] ABSTRACT

An electrochemical detector cell (10) and apparatus incorporating the cell (10) includes a first capillary (12) having an entrance (14) connected to an electrolyte source (30) and an exit (16). A second capillary (18) is connected to reactive gas source (32) and intersects the first capillary (12) at (22) to define a reaction zone (20) in the first capillary (12). A sensor electrode (24) is positioned in the first capillary (12) in the reaction zone (20). A third capillary (26) intersects the first capillary (12) within the reaction zone (20). A reference electrode (28) is positioned in the third capillary (26). The third capillary (26) is connected to a solution source (34). The electrodes (24) and (28) may be used for potentiometric measurements. A fourth capillary (38) intersects the first capillary between entrance (14) and intersection (22) of the first capillary (12) and the second capillary (18). A generator electrode (36) is positioned in the first capillary between the intersection of the fourth capillary (38) and the intersection (22) of the second capillary (18) with the first capillary (12). A counter-electrode (40) to the generator electrode (36) is positioned in the fourth capillary (38).

9 Claims, 4 Drawing Figures

GENERATOR CURRENT

GENERATOR CATHODE

COULOMETER ON

COULOMETER OFF

GENERATOR ANODE

APPARATUS FOR ELECTROCHEMICAL DETECTION AND COULOMETRIC TITRATION

BACKGROUND OF THE INVENTION

1. Field of the Invention

This application relates to an improved electrochemical detector cell design and to an improved electrochemical measuring apparatus incorporating the detector cell design. More particularly, it relates to such a cell design and measuring apparatus applicable to electrochemical detection and measurement methods for many different substances that are electro-active at an electrode or that contribute to electrochemical conductivity in liquids. Most especially, it relates to such an electrochemical detector cell and apparatus in which a substance in a gas stream is converted to an electroactive form by thermal methods and then dissolved in a suitable electrolyte for electrochemical detection. The invention further relates to such an electrochemical detector cell and apparatus in which a first gas or liquid fluid stream is mixed with a second liquid stream, and the constituents of the first stream are detected and measured electrochemically.

2. Description of the Prior Art

Coulson et al. in "Analytical Chemistry," 32, 1245 (1960) reported a titration cell for the continuous and automatic titration of chloride by silver coulometry. An apparatus for titration of chloride as well as other titratable reactants was disclosed in Coulson et al., U.S. Pat. No. 3,032,493, issued May 1, 1962. Improved apparatuses for coulometric titration in similar cells were disclosed by Myers et al., U.S. Pat. No. 3,427,238, issued Feb. 11, 1969, and Coulson, U.S. Pat. No. 3,563,875, issued Feb. 16, 1971. No significant improvements in cells have been made since then over the original Coulson et al. design. Even so, sensitivity is limited by the reagent volume in which the titration is accomplished and by the electrical noise level of the driving circuits.

Despite the absence of further significant development in electrochemical detector cell design, the art pertaining to coulometric titration apparatuses is a well developed one. Examples of such prior art apparatuses are disclosed in Liesch, U.S. Pat. No. 3,305,468, which discloses a batch titrator with interruption before the titration end point; Strickler, U.S. Pat. No. 3,308,041, which discloses a titration cell and apparatus incorporating separated compartments and a mixing funnel in the cell; Wickerham et al., U.S. Pat. No. 3,341,430, which discloses a coulometric titration apparatus with on-off cycling; Dahms, U.S. Pat. No. 3,551,109, which discloses coulometric generation of two species in a batch titration; Linblad et al., U.S. Pat. No. 3,647,668, which discloses a four-electrode coulometric titration cell and apparatus; Muto et al., U.S. Pat. No. 3,846,270, which discloses a membrane flow through coulometric detector cell with three electrodes; Hauser, U.S. Pat. No. 3,912,613, which uses a two-electrode cell with alternating generating and sensing functions; Arawa et al., U.S. Pat. No. 3,950,237, which describes a four-electrode batch type titrator with improved means of integrating the generation current; Fletcher et al., U.S. Pat. No. 4,018,565 describes a four-electrode process titration system with means for automatic introduction of reagents into the titration cell and for circulating titration constituents; Buzza et al., U.S. Pat. No. 4,007,105 which describes a four-electrode cell with amperometric detection; Wilson, U.S. Pat. No. 4,055,478 describes a batch four-electrode titrator with an antilogarithm converter to control the reagent generator current; Mansfield, U.S. Pat. Nos. 4,066,528 and 4,111,776 describes the use of an instrumentation amplifier with a selectable offset bias connected to the sensor and reference electrodes to control the rate of titrant generation in a batch type cell; Victor et al., U.S. Pat. No. 4,118,300 describes a batch four-electrode cell with antilogarithmic control of the generation current; Moore, U.S. Pat. No. 4,133,733 describes a four-electrode coulometric titration cell without provision for continuously changing the electrolyte contained therein; Buzza et al., U.S. Pat. No. 4,170,523 describes a four-electrode batch cell with amperometric sensing electrodes; Ishikawa, U.S. Pat. No. 4,203,156 describes a three-electrode batch type with chopped signal and generator circuits; and Blanke, U.S. Pat. No. 4,230,554 describes a four-electrode batch cell with amperometric sensing electrodes.

Thus, while the art relating to electrochemical detector cells and apparatus incorporating such cells is a well developed one, further improvements are required in order to meet performance demands for certain applications. Such cells need a high level of sensitivity, a rapid response time, and the ability to be convertible for different species to be measured if they are to be employed in combination with gas or liquid chromatographs.

SUMMARY OF THE INVENTION

Accordingly, it is an object of this invention to provide an electrochemical measuring cell and apparatus incorporating the measuring cell of reduced cell volume over prior art cell designs.

It is another object of the invention to provide such a cell and measuring apparatus which operates with a faster recovery time from accidental overloading.

It is still another object of the invention to provide such a cell and measuring apparatus having both sensitivity and selectivity in a variety of measuring applications through use of different electrode surface coatings or electrolyte solutions.

It is yet another object of the invention to provide such a cell and measuring apparatus especially adapted for measurement of components eluted from gas or liquid chromatographs.

The attainment of these and related objects may be achieved through use of the novel electrochemical measuring cell and apparatus incorporating the cell herein disclosed. The cell has a first capillary with an entrance for introducing an electrolyte solution to the cell and an exit for removing the solution from the cell. There is a second capillary for introducing a reactant to the electrolyte solution in the cell. The second capillary intersects the first capillary between the entrance and the exit. The intersection of the second capillary with the first capillary defines a reaction zone for the reactant and the electrolyte in the first capillary. The cell has a sensing electrode in the reaction zone of the first capillary. The cell desirably includes a third capillary intersecting the first capillary in the reaction zone for establishing a solution bridge to the reaction zone. There is a reference electrode in the third capillary positioned to be electrically connected to the reaction zone by the solution bridge. With these two electrodes, the cell of this invention may be employed for potentiometric measurements to determine the amount of the reactant in the electrolyte at the reaction zone.

For use in carrying out coulometric titrations, the cell of this invention may include a fourth capillary intersecting the first capillary between the entrance of the first capillary and the intersection of the first and second capillaries. A third electrode for generating a titrant from the electrolyte in the first capillary is provided in the first capillary between the entrance and the intersection of the first and second capillaries. A fourth counter electrode to the third electrode is positioned in the fourth capillary. In this form of the cell, the electrolyte solution is provided at the entrance of the first capillary at a rate sufficient to supply the reaction zone in the first capillary and to allow excess electrolyte solution to flow out of the fourth capillary.

An electrochemical measuring apparatus incorporating the cell of this invention includes a means for supplying the electrolyte solution to the entrance of the first capillary. There is a means for supplying the reactant to the second capillary, and a means for supplying a solution to the third capillary. Circuit means is connected to the sensing electrode and the reference electrode for measuring a change in electrical property between the electrodes, such as an electrical potential or electrolytic conductivity. In the coulometric titration embodiment of the apparatus, there is also a circuit means connected to the third and fourth electrodes for supplying a titrant generating current through the third and fourth electrodes.

In operation of the cell and apparatus of this invention, the small volume of the cell resulting from the use of capillaries to form the cell and the high degree of physical separation between the electrodes serving different functions in the cell results in a rapid response time, faster recovery from accidental overloading, increased sensitivity resulting from low electrical noise, and related benefits. While these features make the cell and apparatus of this invention especially suitable for measurement of components eluted from gas or liquid chromatographs, these desirable features of the cell and apparatus of this invention should make it useful in a wide variety of other analytical applications as well.

The attainment of the foregoing and related objects, advantages and features of the invention should be more readily apparent to those skilled in the art, after review of the following more detailed description of the invention, taken together with the drawings, in which:

DETAILED DESCRIPTION OF THE INVENTION

Figure 1:
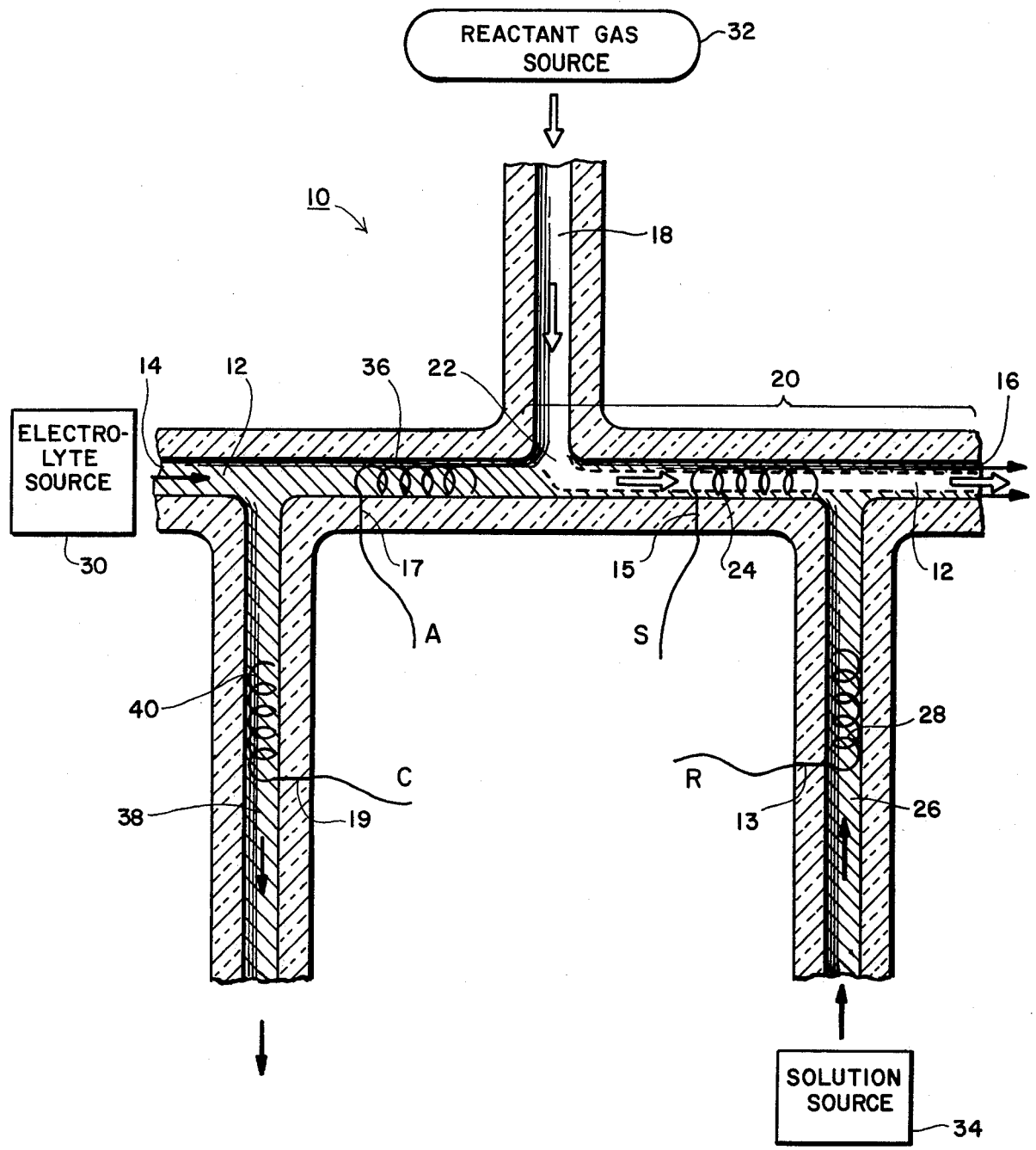
FIG. 1 is an enlarged cross sectional view of a cell in accordance with the invention for an electrochemical measuring apparatus.

Turning now to the drawings, more particularly to FIG. 1, there is shown a cell 10 suitable for carrying out both potentiometric measurements and coulometric titrations. The cell 10 is formed from Pyrex glass or other similar dielectric material. A first capillary 12 extends horizontally from left to right across the cell 10. The first capillary 12 has an entrance 14 for an electrolyte solution and an exit 16 for the solution. A second capillary 18 intersects the first capillary 12, approximately midway between the entrance 14 and the exit 16 at right angles, to define a reaction zone 20 between the intersection 22 and the exit 16 from the first capillary 12. Coiled electrode 24 is positioned longitudinally in the reaction zone 20, along with the first capillary 12. A third capillary 26 intersects the first capillary 12 at right angles, between the first electrode 24 and the exit 16 from the first capillary 12. A second coiled electrode 28 is positioned longitudinally in the third capillary 26.

In use of the cell 10 for making potentiometric measurements, the entrance of the first capillary 12 is connected to an electrolyte source 30. The second capillary 18 is connected to a reactant gas source 32. The third capillary 26 is connected to a solution source 34, in order to establish a solution bridge between the first and second electrodes 24 and 28. In practice, the reactant gas source 32 may be a reactor tube, such as a pyrolysis tube for preconditioning the reactant in a reducing atmosphere, such as hydrogen gas, which may also contain a catalyst, such as nickel; a pyrolysis tube for preconditioning of the reactant in an oxidizing atmosphere, such as oxygen or air, which may also contain a catalyst, such as platinum; a photoionization tube in which chemical compounds are photochemically decomposed, a gas chromatographic column through any of the above reactor tubes; a pyrolysis tube furnace into which discrete samples are introduced; or the like.

With the elements of the detector cell 10 described so far, it is possible to carry out potentiometric measurements, utilizing the electrodes 24 and 28 to determine electrochemical potential induced by the electrolyte solution supplied at entrance 14 and the reactant gas supplied through capillary 18, when they react in the reaction zone 20. Circuitry for obtaining these potentiometric measurements is described below.

For use in coulometric titrations, a third, titrant generator electrode 36 is provided in the first capillary 12, between the entrance 14 and the intersection 22 of the first and third capillaries 18. A fourth capillary 38 intersects the first capillary 12 at right angles between the entrance 14 and the third electrode 36. A fourth, counter-electrode 40 to the third electrode 36 is provided in the fourth capillary 38. The flow of electrolyte from source 30 into first capillary 12 is sufficient both to provide a continuous flow of the electrolyte beyond the intersection of the first and fourth capillaries, as well as allowing a continuous flow of the electrolyte in the fourth capillary. As a result, a solution bridge is established between the third electrode 36 and the fourth electrode 40 and reaction products from the fourth electrode are not allowed to enter the reaction zone.

In operation, current is supplied to the third electrode 36 for causing an electrochemical reaction with a component of the electrolyte solution to produce a titrant for the reactant gas. Circuitry for supplying the current for electrode 36 as well as for making the coulometric titration measurements will be explained below.

In practice, the electrodes 24, 28, 36, and 40 are formed from platinum wire, another wire plated with platinum, platinum coated with an electro-active metal, such as silver, or from gold, or the like. The capillaries 12, 18, 26, and 38 desirably have a diameter of from about 0.1 to about 3 millimeters, preferably a diameter of about 1 millimeter. The capillary intersections should be sharp and not enlarged to insure smooth and continuous flow. Liquid flow rates in the capillaries 12, 26, and 38 are varied between 0.1 and 10 milliliter/minute for one millimeter diameter capillaries, and correspondingly higher or lower for larger or smaller capillaries, respectively.

Figure 2:
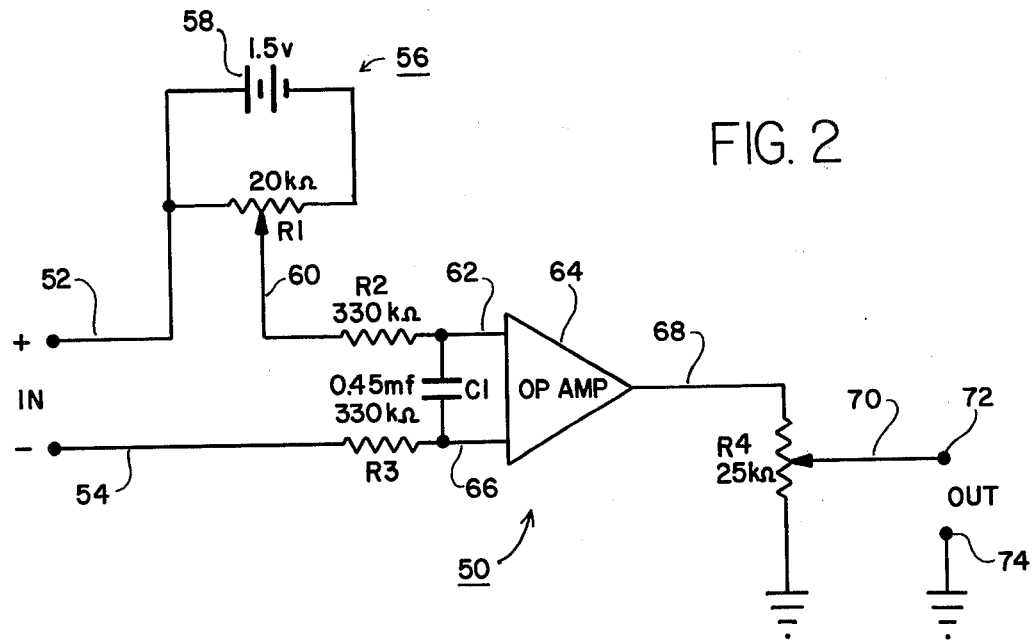
FIG. 2 is a schematic diagram of circuitry suitable for use with the cell of FIG. 1.

FIG. 2 is a schematic diagram of a circuit 50 for measuring the potential difference between the sensor electrode 24 and the reference electrode 28 in the electrochemical detector cell 10 of FIG. 1. Line 52 of the circuit is connected to sensing electrode 24 by lead 15 (FIG. 1) and line 54 is connected to reference electrode 28 by lead 13. Line 52 is connected to bias circuit 56, which consists of battery 58 and voltage divider potentiometer R1. Line 60 connects the potentiometer R1 through resistor R2 and line 62 to one input of operational amplifier 64. Line 54 is connected through resistor R3 and line 66 to the other input of operational amplifier 64. Lines 62 and 66 are coupled by capacitor C1. The output of operational amplifier 64 is connected by line 68, voltage divider potentiometer R4 and line 70 to output terminal 72. Output terminal 74 and potentiometer resistor R4 are also grounded. Output terminals 72 and 74 of the circuit 50 are connected to a strip chart recorder or other suitable means for recording outputs from the circuit 50.

Figure 3:
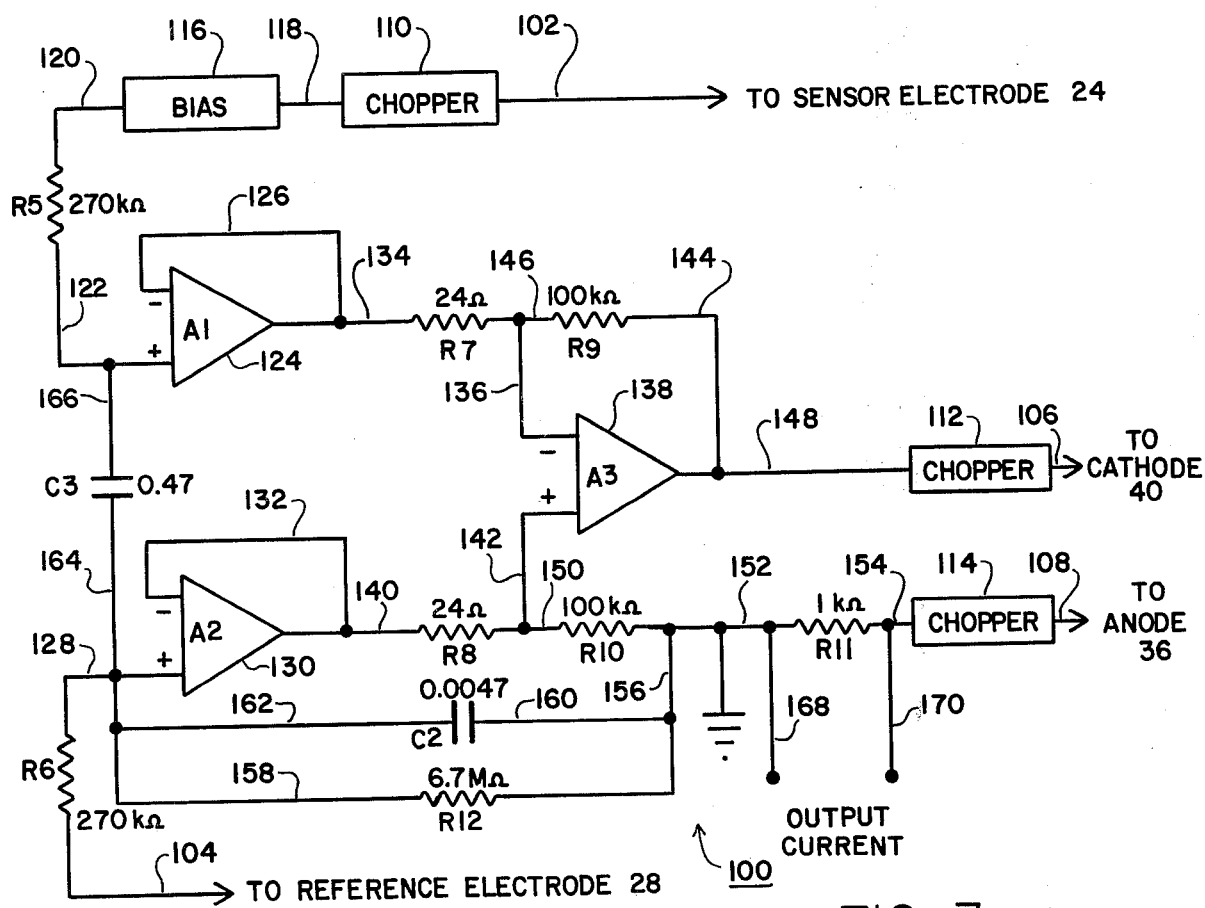
FIG. 3 is a schematic diagram of additional circuitry suitable for use with the cell of FIG. 1.

FIG. 3 is a schematic diagram of a circuit 100 for use with the electrochemical detector cell 10 of FIG. 1 for continuous coulometric titration of electro-active substances in a flowing fluid stream in the reaction zone 20 of the cell. Electrode 24 of the cell is connected by lead 15 (FIG. 1) to line 102 of the circuit 100. Line 104 is connected by lead 13 to the reference electrode 28 of the cell 10. Lines 106 and 108 are respectively connected by leads 17 and 19 to the electrodes 40 and 36 of the cell. The lines 102, 106, and 108 are respectively connected to choppers 110, 112, and 114. The choppers 110, 112, and 114 are preferably implemented as light emitting diode (LED) switches. In the normal operation of the coulometric circuit 100, chopper 110 passes the signal on line 102, while choppers 112 and 114 block passage of signals to lines 106 and 108, and vice versa. Chopper 110 is connected to bias circuit 116 by line 118. Bias circuit 116 is connected by line 120, resistor R5, and line 122 to the positive input terminal of operation amplifier 124. The output of operational amplifier 124 is supplied as a feedback input to the negative input of the amplifier by line 126. Line 104 is connected through resistor R6 and line 128 to the positive input of operational amplifier 130. The output of operational amplifier 130 is connected as a feedback to the negative input terminal of the operational amplifier by line 132. The output of operational amplifier 124 is supplied on line 134 through resistor R7 and on line 136 to the negative input terminal of operational amplifier 138. The output of operational amplifier 130 is supplied on line 140 through resistor R8 and on line 142 to the positive input terminal of operational amplifier 138. The output of operational amplifier 138 is supplied by line 144 through resistor R9 and lines 146 and 136 as a feedback input to operational amplifier 138. The output of operational amplifier 138 is also supplied on line 148 to chopper 112. The output of operational amplifier 130 is also supplied on line 150, through resistor R10, line 152, through resistor R11, and line 154 to chopper 114. Line 152 is also connected by lines 156, resistor R12, line 158, line 160, capacitor C2 and line 162 to positive input to operational amplifier 130. Lines 128 and 122 are also connected by line 164, capacitor C3 and line 166. The output current or generator current supplied by the circuit 100 to anode 36 is monitored by measuring the voltage across resistor R11 by connecting output lines 168 and 170 to a recording instrument, such as a strip chart recorder. The voltage gain from the coulometric circuit containing operational amplifiers 124, 130, and 138 is from about 1,000 to about 30,000. The choppers 110, 112, and 114 limit electrical noise, and may be omitted if desired.

Figure 4:
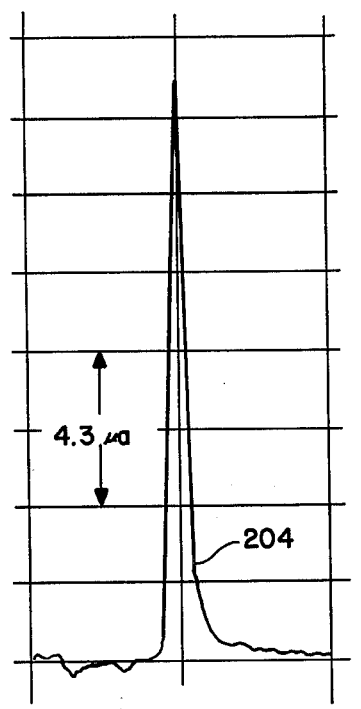
FIG. 4 is a set of potentiometric and coulometric curves obtained with use of the cell of FIG. 1 with the circuitry of FIGS. 2 and 3.
Figure 4:
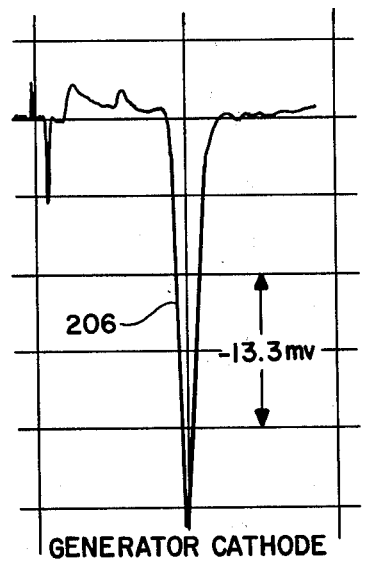
Figure 4:
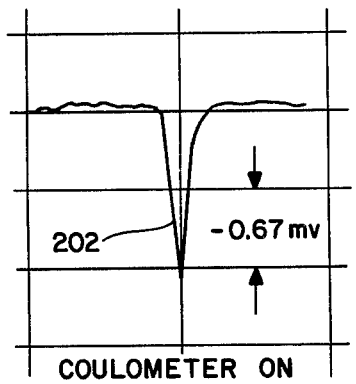
Figure 4:
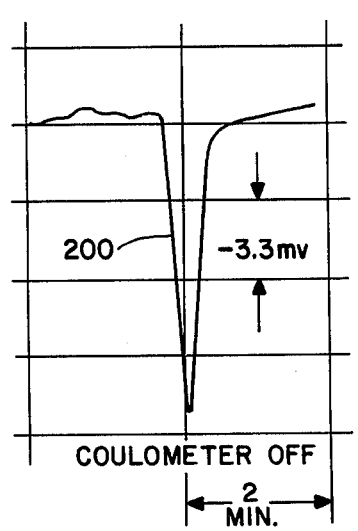
Figure 4:
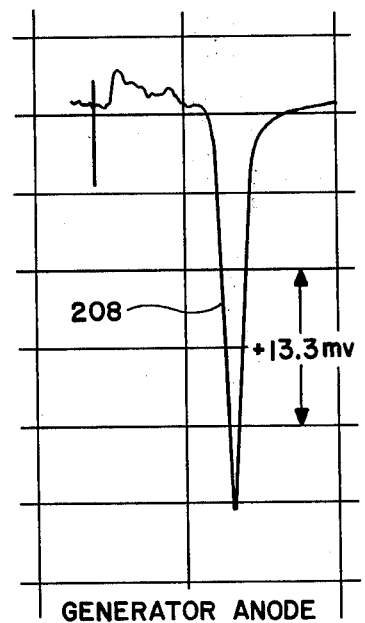

FIG. 4 shows representative electrode potentials measured with the potentiometric circuit of FIG. 2 for the generator electrodes 36 and 40 and the sensor electrode 24, all measured against the reference electrode 26, and the coulometric current generated with the coulometric circuit 100 for five identical gas chromatograms for diethyl sulfide. Curve 200 was measured with the coulometer electrodes 36 and 38 disconnected from the circuit 100. Curves 202, 204, 206, and 208 were all measured with the electrodes 36 and 38 connected to the circuit 100 in the normal manner, and the potentiometric circuit 50 connected to various electrodes. The area under curve 204 represents the number of coulombs required to titrate the sulfur dioxide resulting from the oxidative pyrolysis of the gas chromatographic effluent followed by introduction of the pyrolysis products into the electrochemical detector cell. The electrolyte contained iodide and a trace of iodine. Additional iodine was generated at electrode 36 as required to titrate the $SO_2$ in the gas stream entering the cell through capillary 18.

The titration reaction was $$SO_2 + 2H_2O + I_3^- \rightarrow SO_4^= + 3I^- + 4H^+ \qquad (1)$$

Other reactions that are operable with the coulometric titrator are:

$$Cl^- + Ag^+ \rightarrow AgCl \qquad (2)$$

$$2Cl^- + 2Hg^+ \rightarrow Hg_2Cl_2 \qquad (3)$$

$$Br_2 + 3I^- \rightarrow I_3^- + 2Br^- \qquad (4)$$

In the case of reaction (4) generator electrode 36 is polarized as a cathode to remove $I_3^-$ as needed to maintain the sensor electrode 24 potential at a preselected value. In reactions (1), (2), and (3), generator electrode 36 is polarized as an anode to produce $I_3^-$, $Ag^+$, or $Hg^+$, respectively, as needed to maintain the sensor electrode 24 at a preselected value.

It should now be readily apparent to those skilled in the art that an electrochemical detector cell and an analytical apparatus incorporating the cell capable of achieving the stated objects of the invention has been provided. Greater sensitivity is obtainable with the cell of this invention than with prior art cells, due to the small volume of solution in which the measurements are made. The cell operates in a flow-through mode, so it can recover quickly from accidental overloading with electroactive substances. The cell has great flexibility in applications for sensitive and selective measurements resulting from change in electrode surface coatings or electrolyte solutions. Intracell electrical effects resulting from IR-drop in solution are essentially eliminated by physical separation of generator electrodes 36 and 38 from the sensor and reference electrodes 24 and 28 by means of the capillaries. As a result the cell and apparatus are especially suited for the analysis of components eluted from gas or liquid chromatographs. Examples of analyses that can be carried out with the cell and apparatus of this invention include pesticides in foods, haloforms and other chlorinated or brominated organic compounds in drinking water, sulfur compounds in petroleum and petroleum products, toxic organic vapors in samples collected in work place environments, and the like. Many other applications will occur to analytical chemists.

It should further be apparent to those skilled in the art that various changes in form and details of the invention as shown and described may be made. It is intended that such changes be included within the spirit and scope of the claims appended hereto.

What is claimed is:

1. A cell for an electrochemical measuring apparatus, which comprises means defining a first capillary tube having an entrance end for introducing an electrolyte solution to said cell and an exit end for removing the solution from said cell, means defining a second capillary tube for introducing a reactant to the electrolyte solution in said cell, said second capillary tube intersecting said first capillary tube between the entrance and the exit ends to define a reaction zone for the reactant and the electrolyte in said first capillary tube at said point of intersection and extending downstream thereof, means defining a third capillary tube intersecting said first capillary tube in the reaction zone downstream of the intersection of said first and second capillary tubes near the exit end for establishing a solution bridge to the reaction zone, a sensing electrode in the reaction zone of said first capillary tube immediately downstream of the intersection of said first and second capillary tubes and upstream of the intersection of said first and third capillary tubes, a reference electrode positioned within the bore of said third capillary tube to be electrically connected to the reaction zone by the solution bridge, said electrodes being contoured to the internal surface of the bore and positioned to contact the solution within the bore of the respective capillary tubes and allowing unobstructed flow therethrough.

2. An electrochemical measuring apparatus which comprises the cell of claim 1, means for supplying the electrolyte solution to the entrance end of said first capillary tube, means for supplying the reactant to said second capillary tube, means for supplying a solution to said third capillary tube, and circuit means connected to said sensing electrode and said reference electrode for measuring a change in electrochemical property between said electrodes.

3. The cell of claim 1 additionally comprising a fourth capillary tube intersecting said first capillary tube between means defining the entrance end of said first capillary tube and the intersection of said first and said second capillary tubes, a third electrode within the bore of said first capillary tube between the intersection of said first and fourth capillary tubes and the intersection of said first and second capillary tubes, for generating a titrant from the electrolyte and a fourth counter-electrode to said third electrode, said fourth electrode being positioned within the bore of said fourth capillary tube.

4. An electrochemical measuring apparatus, which comprises the cell of claim 3, means for supplying the electrolyte solution to the entrance end of said first capillary tube at a rate sufficient to supply the reaction zone in a continuous flow and to allow the electrolyte solution to flow out of said fourth capillary tube in a continuous flow to establish a solution bridge between said third and fourth electrodes and for preventing reaction products from said fourth electrode from entering the reaction zone, means for supplying the reactant to said second capillary tube, means for supplying a solution to said third capillary tube to form a solution bridge between said first and second electrodes, circuit means connected to said sensing electrode and said reference electrode for measuring an electrical potential difference between each said sensing and reference electrodes, and circuit means connected to said third and fourth electrodes for supplying a titrant generating current to said third electrode.

5. The electrochemical measuring apparatus of claim 4, additionally comprising a titrant generator current measuring circuit connected to said titrant generating current circuit means.

6. The electrochemical measuring apparatus of claim 4 additionally comprising a first chopper connected between said sensor electrode and said electrical potential measuring circuit means for alternately connecting and disconnecting the sensor electrode and said electrical potential measuring circuit means, and second and third choppers respectively connected between said third and fourth electrodes and said titrant generating current circuit means.

7. The electrochemical measuring apparatus of claim 4 in which said reactant supplying means is a reactor tube.

8. The electrochemical measuring apparatus of claim 7 in which the reactor tube is a pyrolysis tube.

9. The electrochemical measuring apparatus of claim 7 additionally comprising a gas chromatographic column connected to the reactor tube.

* * * * *